US008610057B2

United States Patent
Atkinson et al.

(10) Patent No.: US 8,610,057 B2
(45) Date of Patent: *Dec. 17, 2013

(54) ION SELECTION APPARATUS AND METHOD (75) Inventors: Jonathan Richard Atkinson, Watford (GB); Alastair Clark, Watford (GB); Bruce Alec Colin Grant, London (GB); Robert Brian Turner, Chesham (GB)

(73) Assignee: Smith Detection-Watford Limited, Watford Herts (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,526

(22) Filed: Jul. 6, 2011

(65) Prior Publication Data
US 2011/0260053 A1    Oct. 27, 2011

Related U.S. Application Data (63) Continuation of application No. 12/160,413, filed as application No. PCT/GB2007/000021 on Jan. 9, 2007, now Pat. No. 7,977,627.

(30) Foreign Application Priority Data

| Jan. 10, 2006 | (GB) | 0600362.8 |
| Jun. 16, 2006 | (GB) | 0611935.8 |
| Sep. 23, 2006 | (GB) | 0618788.4 |

(51) Int. Cl.
*H01J 49/40* (2006.01)

(52) U.S. Cl.
CPC ..................... *H01J 49/40* (2013.01)
USPC ......................................................... 250/287

(58) Field of Classification Search
None
See application file for complete search history.

(56) References Cited

U.S. PATENT DOCUMENTS

| 5,200,614 | A | 4/1993 | Jenkins |
| 7,105,808 | B2 | 9/2006 | Bromberg et al. |
| 7,378,651 | B2 * | 5/2008 | Guevremont ................. 250/287 |
| 7,977,627 | B2 * | 7/2011 | Atkinson et al. .............. 250/287 |
| 2006/0049363 | A1 | 3/2006 | Guevremont |
| 2010/0258715 | A1 | 10/2010 | Turner et al. |
| 2010/0314548 | A1 | 12/2010 | Munchmeyer et al. |

FOREIGN PATENT DOCUMENTS

| GB | 2 413 213 A | 10/2005 |
| WO | WO-2004/102178 A1 | 11/2004 |
| WO | WO-2005/059518 A2 | 6/2005 |

OTHER PUBLICATIONS

International Search Report dated Mar. 19, 2007 from corresponding International Application PCT/GB2007/000021 (3 pgs.).
Office Action in U.S. Appl. No. 12/160,413 dated Oct. 22, 2010.
US Notice of Allowance in U.S. Appl. No. 12/160,413 dated Mar. 7, 2011.

\* cited by examiner

*Primary Examiner* — Jack Berman
(74) *Attorney, Agent, or Firm* — Foley & Lardner LLP (57) ABSTRACT

An ion mobility spectrometer or other ion apparatus has two or three grid electrodes 51 and 52; 151 to 153; 106 and 107; 106' and 107' extending laterally of the ion flowpath. An asymmetric waveform with a dc compensating voltage is applied between the electrodes to produce a field parallel to the ion flow path that affects ions differently according to their field-dependent mobility. This filters or delays different ions selectively in their passage to an ion detector 11, 111, 111' to facilitate discrimination between ions that would otherwise produce a similar output.

24 Claims, 6 Drawing Sheets

though or partially through the ion flow path is dependent on the mobility of the ions.

ION SELECTION APPARATUS AND METHOD

CROSS-REFERENCE TO RELATED PATENT APPLICATIONS

This application is a Continuation of U.S. application Ser. No. 12/160,413, filed Jul. 9, 2008 as the National Stage of PCT/GB2007/000021, filed Jan. 9, 2007, which claims priority to United Kingdom Application 0600362.8, filed Jan. 10, 2006, including the specification, drawings, claims and abstract, is incorporated herein by reference in its entirety; United Kingdom Application 0611935.8, filed Jun. 16, 2006, including the specification, drawings, claims and abstract, is incorporated herein by reference in its entirety; and United Kingdom Application 0618788.4, filed Sep. 23, 2006, including the specification, drawings, claims and abstract, is incorporated herein by reference in its entirety.

BACKGROUND OF THE INVENTION

This invention relates to ion selection apparatus of the kind including means for providing ions along a path.

Ion mobility spectrometer (IMS) systems are often used to detect substances such as explosives, drugs, blister and nerve agents or the like. An IMS system typically includes a detector cell to which a sample of air containing a suspected substance is supplied as a gas or vapour. The cell operates at or near atmospheric pressure and contains electrodes energized to produce a voltage gradient along the cell. Molecules in the sample of air are ionized, such as by means of a radioactive source, UV source or by corona discharge, and are admitted into the drift region of the cell by an electrostatic gate at one end. The ionized molecules drift to the opposite end of the cell at a speed dependent on the size of the ion. By measuring the time of flight along the cell it is possible to identify the ion.

In a field asymmetric IMS or FAIMS, the ions passed by the gate are admitted to a gap between two closely-spaced electrodes aligned parallel with the axis of the apparatus and the path of travel of the ions. An asymmetric field is applied across the gap, which causes the ions to be drawn laterally alternately to one or other of the electrodes. Depending on the mobility of the ions they will either hit one of the electrodes and be neutralized or pass through the gap for detection. By altering the asymmetric field, or a dc bias voltage superimposed on this, the apparatus can be tuned to select for specific ions. There are various problems with FAIMS systems. They can be difficult to use with ionization sources that produce predominantly ions of a single polarity, such as corona discharge devices. This is because some of the ions produced by such devices tend to collect on insulated surfaces in front of the FAIMS gap and build up a charge on such surfaces. This reduces the number of like polarity ions entering the gap and can reduce the ability of the FAIMS apparatus to detect some substances.

It is an object of the present invention to provide an alternative ion selection apparatus and method.

According to one aspect of the present invention there is provided ion selection apparatus of the above-specified kind, characterised in that the apparatus includes first and second parallel electrodes spaced from one another along the path and extending laterally across the path, the electrodes being arranged to allow passage of ions through them, and an arrangement for applying an asymmetric voltage across the two electrodes to create in the gap between the electrodes periods of a high field followed by longer periods of a low field such that some of the ions pass through the two electrodes and others of the ions do not pass through the two electrodes.

The apparatus preferably includes an arrangement for applying a compensation voltage to control passage of ions through the electrodes. The electrodes may be provided by wire grids with spaces between the wires through which the ions can pass.

According to another aspect of the present invention there is provided ion selection apparatus including means for providing ions along a path, characterised in that the apparatus includes an electrode arrangement extending laterally of the path, the electrode arrangement allowing passage of selected ions through it, an arrangement for applying an asymmetric voltage across the electrode arrangement to create in the electrode arrangement periods of a high field followed by longer periods of a low field, and an arrangement for applying a compensation voltage to the electrode arrangement such that only ions having a differential mobility greater than a first predetermined value and less than a second predetermined value pass through the electrode arrangement.

The electrode arrangement may include three parallel electrodes, the asymmetric voltage being applied to the middle electrode and two compensating voltages being applied to the outer electrodes.

According to a further aspect of the present invention there is provided a method of selecting ions in a region along a path of travel of the ions, characterised in that the method includes providing an electrical field parallel to the path, and that the field comprises periods of a high field followed by longer periods of a low field such that only selected ones of the ions are passed through the field.

The field preferably includes a dc compensation field selected such that only selected ones of the ions are passed through the field.

According to a fourth aspect of the present invention there is provided an ion mobility spectrometer including an ion source, a drift region, and a detector for detecting ions passing along the drift region, characterised in that the spectrometer includes an arrangement for selecting ions including first and second parallel electrodes spaced from one another along the length of the spectrometer and extending across the path of ions, that the electrodes are arranged to allow passage of ions through them, and an arrangement for applying an asymmetric voltage across the two electrodes to create in the gap between the electrodes periods of a high field followed by longer periods of a low field such that only selected ones Of the ions are passed through the drift region.

The ion mobility spectrometer may include a gate for gating passage of ions to the detector, the first and second parallel electrodes being located upstream of the gate so that only ions selected by the electrodes are passed to the gate. The voltage applied to the electrodes may be selected to allow passage of ions from one species and to prevent passage of ions from another species where the two species would normally produce similar outputs from the spectrometer. The apparatus may include an arrangement for applying a low field to a region between the detector and the arrangement for applying the asymmetric field.

According to a fifth aspect of the present invention there is provided apparatus including a source of ions, an ion detector and an ion flow path extending between the source and the detector, characterised in that the apparatus includes an arrangement for applying an asymmetric electric field substantially parallel to the ion flow path along a part at least of the ion flow path such that ions flowing along the path are subjected to alternate high and low fields such that the time taken for an ion to reach the detector is dependent on the difference between its low field mobility and its high field mobility.

The asymmetric field is preferably applied between two parallel grid electrodes extending at right angles to the ion flow path and spaced from one another along the path.

According to a sixth aspect of the present invention there is provided a method of providing information about ions including the steps of supplying the ions along an ion flow path towards an ion detector, subjecting the ions to an asymmetric electric field substantially parallel to the ion flow path along a part at least of the ion flow path such that ions flowing along the path are subjected to alternate high and low fields, measuring the time taken for ions to reach the detector and providing information about the ions in accordance with the measured time taken to reach the detector.

An IMS system according to the present invention, will now be described, by way of example, with reference to the accompanying drawings, in which.

Figure 1:
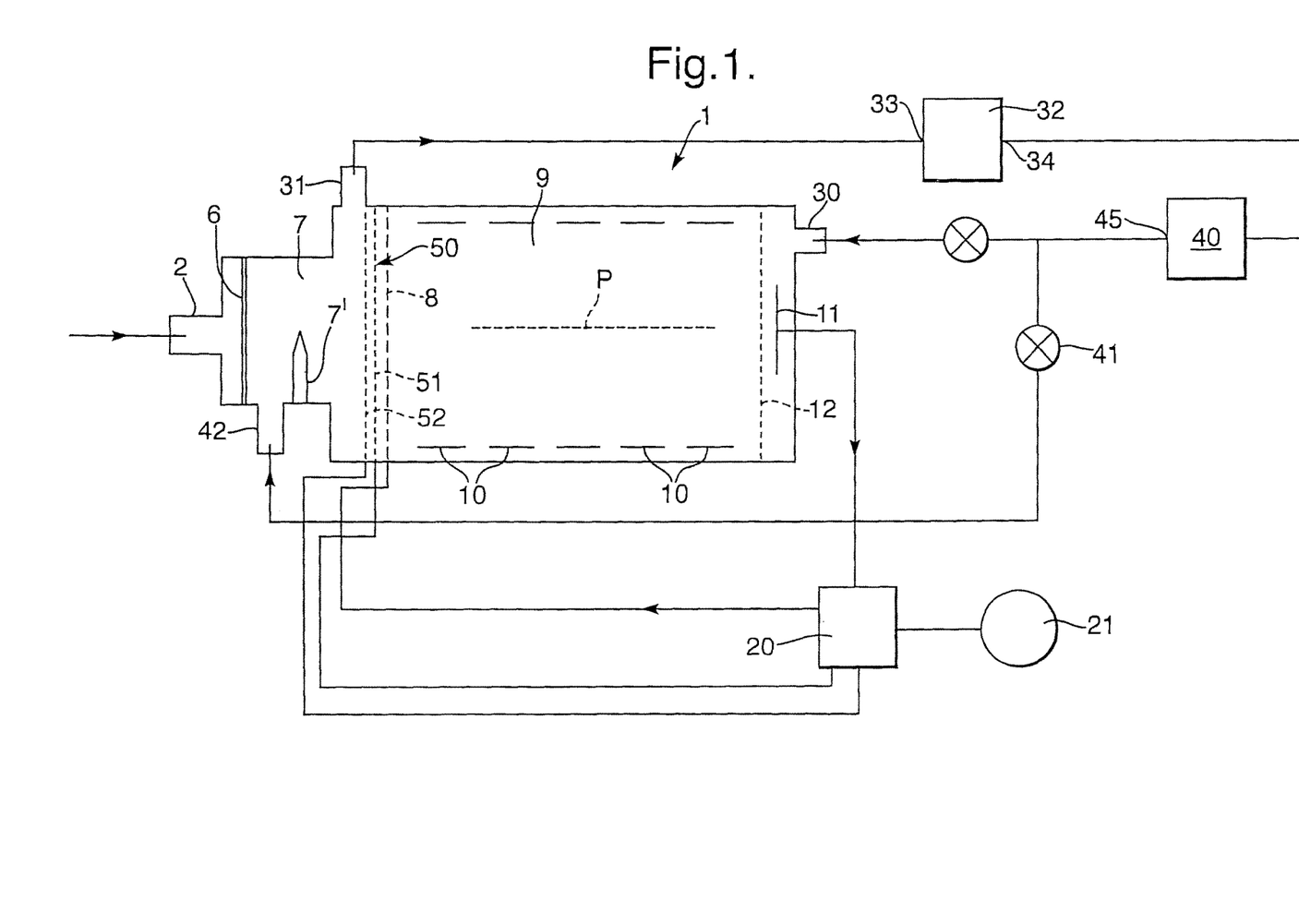
FIG. 1 shows the system schematically.
Figure 2:
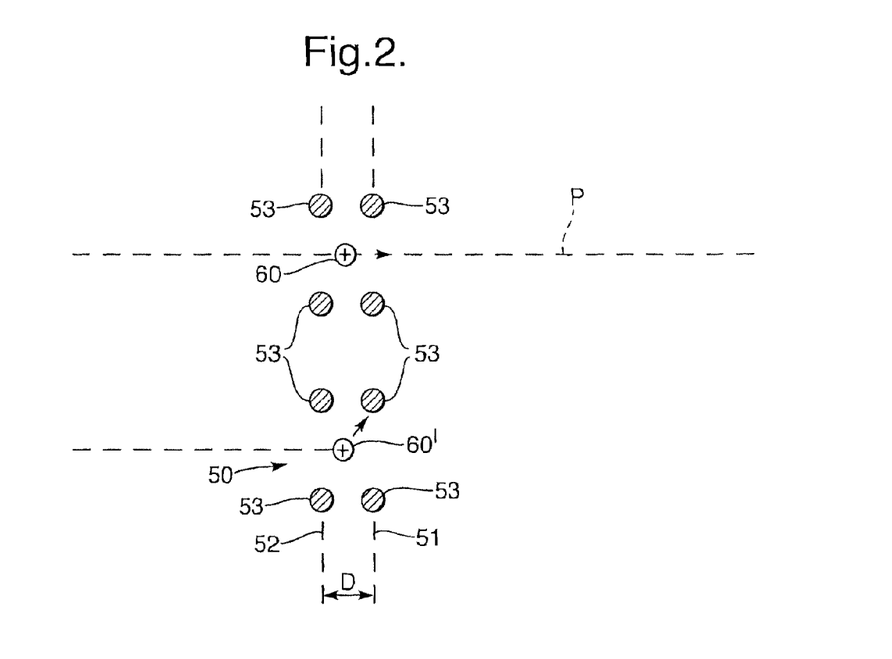
FIG. 2 shows a part of the ion filter of the system of FIG. 1 to a larger scale.

With reference first to FIGS. 1 and 2, the system includes an IMS drift cell 1 having an inlet port 2 by which sample air to be analysed is supplied to the apparatus. The port 2 opens into the left-hand end of the interior of the cell 1 via a selective barrier 6 such as a semi-permeable membrane, or of any other form that allows passage of the molecules of interest whilst excluding the majority of other molecules. Alternatively, the barrier 6 could be non-selective, such as a pinhole, as described in W093/0 1485. Instead of a barrier, the sample to be analysed may be supplied to the cell 1 by some other interface, such as of the kind described in EP596978.

The barrier 6 communicates with an ionisation region 7 including an ionisation source such as a corona discharge needle 7', which produces predominantly ions of a single polarity, positive or negative. Other ionisation sources could be used, such as a radioactive isotope, such as $^{63}$Ni or $^{241}$Am, or a source of photons, such as a laser, to produce ions by photoionisation. To the right of the ionisation region 7 a Bradbury Nielson gating grid 8 controls passage of ionised molecules into a drift region 9 formed by a series of drift electrodes 10. The ions are caused to move from left to right, from the ionisation region 7 to the gate 8 by means of an applied electric field or by a flow of gas from left to right. A collector or detector plate 11 at the right-hand end of the cell 1 collects ions passed through the drift region 9. A screen grid 12 is located close in front of the collector plate 11 and is held at an appropriate potential so that it shields the plate 11 from the image charge that would otherwise be generated by the incoming ions. The plate 11 provides an output to a processor or control unit 20, which also controls the gate 8 and various other functions of the system. The processor 20 provides an output to a display 21, or other utilisation means, indicative of the nature of the sample.

At its right-hand end, the cell 1 has an inlet 30, by which recirculated, cleaned, dried drift gas is supplied to the interior of the cell where it travels from right to left and flows out via an exhaust outlet 31 close to the gating grid 8 in the ionisation region 7. Air is supplied to the inlet 30 by means of a pump 32 having an inlet 33 connected to the exhaust outlet 31 and an outlet 34 connected to a molecular sieve 40, which cleans and dries the air exhausted from the drift chamber 9. The outlet 45 of the sieve 40 also connects via a valve 41 to an inlet 42 just downstream of the membrane 6 so that a source of clean air is circulated and mixes with the analyte vapours diffusing through the membrane.

The system differs from previous IMS systems by the inclusion of an arrangement 50 located adjacent and upstream of the gate 8 to alter the flow of ions along the apparatus. In the arrangement shown in FIGS. 1 and 2, this acts as ion selection means or an ion filter.

The ion filter 50 comprises two electrodes 51 and 52 arranged at right angles to the length of the apparatus and to the path P of travel of the ions 60. The two electrodes 51 and 52 extend across the path P of travel of the ions 60 so that all ions passed by the gate 8 must first pass through the electrodes. The construction of the electrodes 51 and 52 is such as to permit passage of ions through them, that is, they include gaps or apertures through which the ions can pass. In the present example, each electrode 51 and 52 is formed by a grid of closely-spaced parallel wires 53. The angular orientation of the wires in the two electrodes 51 and 52 is not critical; they could be at any angle from parallel to at right angles but, in the present example they are aligned parallel. Typically, the wires 53 in each grid 51 and 52 are 0.02 mm in diameter and are spaced from one another by 0.1 mm. The two electrode grids 51 and 52 are parallel and are spaced from one another by 0.5 mm.

This ion selection arrangement is not confined to application with ion mobility spectrometers but could be used with other detectors or in other arrangements where ions need to be selected.

Figure 3:
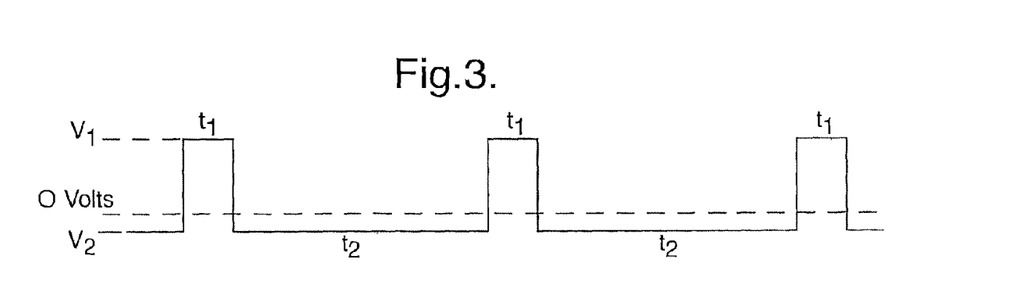
FIG. 3 is a graph showing the voltage applied to the ion filter.

The processor 20 applies a voltage across the two electrode grids 51 and 52 of the kind shown in FIG. 3. The voltage is asymmetric comprising short periods $t_1$ of relatively high voltage $V_1$ and longer intervals $t_2$ of relatively low voltage $V_2$ of opposite polarity. The net field, integrated over at least one cycle is zero. A DC compensation voltage is superimposed on the asymmetric field to oppose or reinforce motion of the ions. By adjusting this compensation voltage, the differential mobility cut-off point can be set where desired. The differential mobility is the difference between the value of the low field mobility and the high field mobility. All ions having a differential mobility greater than the minimum required will eventually pass through.

If the mobility at the low field $E_1$ is $K_1$ and that the mobility at the high field $E_2$ is $K_2$ and the asymmetric waveform is such that the time at the high voltage $V_1$ is $t_1$ and the time at low voltage $V_2$ is $t_2$ then the frequency of the asymmetric waveform is $1/(t_1+t_2)$ and the net distance travelled in one waveform cycle is:

$$S = K_1 \cdot E_1 \cdot t_1 + K_2 \cdot E_2 \cdot t_2$$

If the gap between the electrodes 51 and 52 is D and the compensation voltage is C then:

$$E_1=(V_1+C)/D \text{ and } E_2=(V_2+C)/D$$

For an ion to pass through such a device after N waveform cycles:

$$N \cdot S >= D$$

or $$N\{K_1 \cdot t_1((V_1+C)/D)+K_2 \cdot t_2((V_1+C)/D\} >= D$$

which rearranged gives:

$$N\{K_1 \cdot t_1((V_1+C)/D^2)+K_2 \cdot t_2((V_1+C)/D^2)\} >= 1$$

Figure 4:
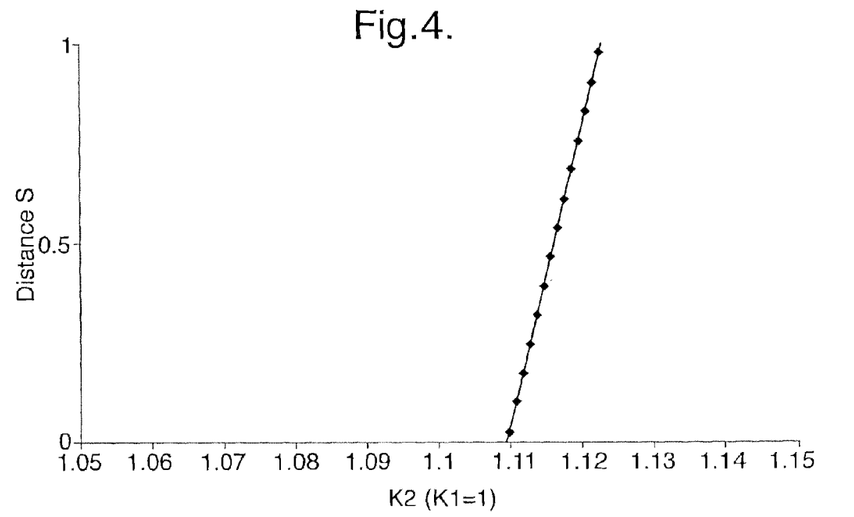
FIG. 4 is a graph showing the distance travelled by ions with different high field mobilities with a first waveform polarity.

The behaviour indicated by this simple model is shown in the graph in FIG. 4. This shows the distance S travelled by an ion in a certain number of rf cycles plotted against its high field mobility $K_2$. The low field mobility $K_1$ has been set to be 1 and a compensation voltage C has been applied.

With a device having a gap D between the grids of 1 then, under these conditions, all ions that have $K_2$ greater than about 1.125 will pass through the device.

The slope of the line in the graph of FIG. 4 is dependent on the time allowed to the ions. Under ideal conditions the line would be orthogonal to the $K_2$ axis.

Figure 5:
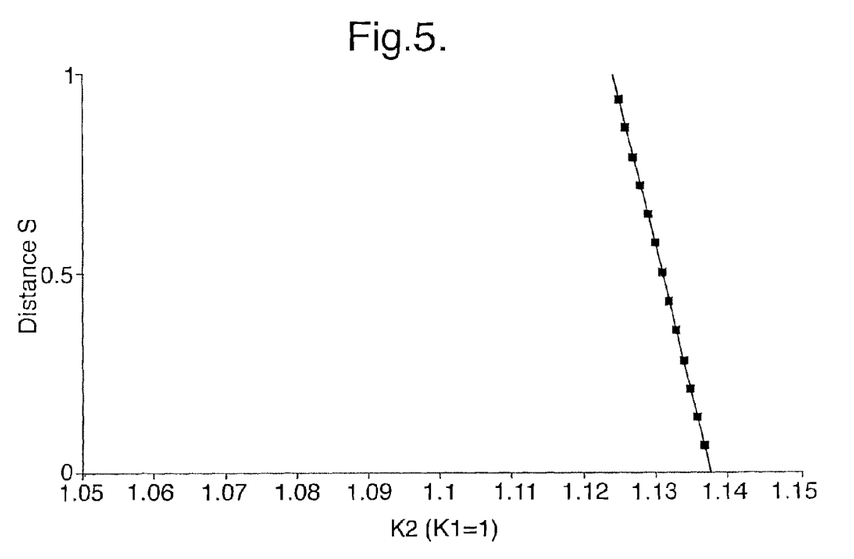
FIG. 5 is a graph showing the distance travelled by ions with different high field mobilities with a second, opposite waveform polarity.

In the above example, the compensation voltage C is set to oppose the motion of the ions caused by differential mobility. Alternatively, the polarity of the waveform could be reversed so that the differential mobility effect tends to stop the ions passing through the far grid 51. Application of an appropriate compensation voltage C would then result in a different situation. In this situation, ions with a differential mobility less than a certain magnitude would get through. The graph shown in FIG. 5 illustrates this situation. Ions with a $K_2$ less than about 1.126 will pass through.

Figure 6:
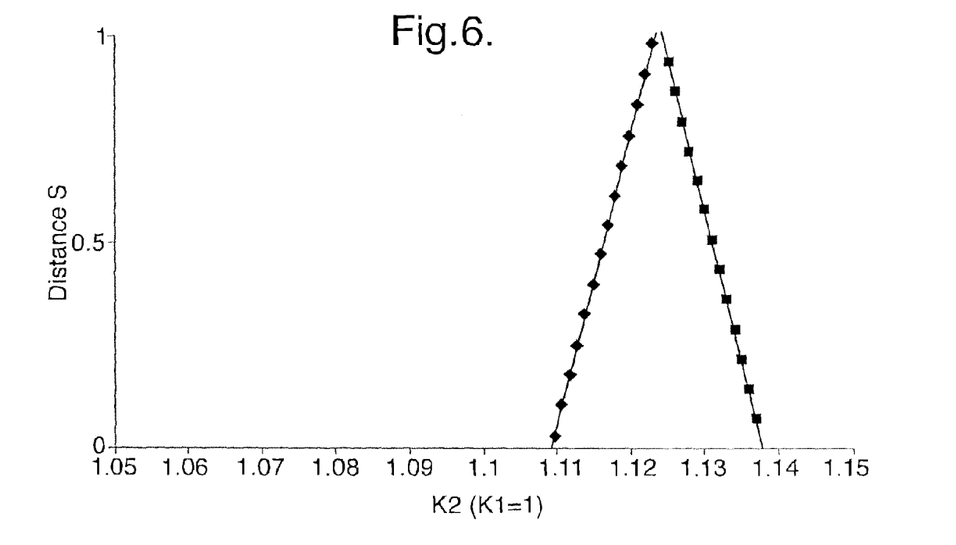
FIG. 6 is a graph showing the combination of the arrangements shown in FIGS. 4 and 5.

These two arrangements could be combined to produce a combined system with a pass-band of high field mobilities, as shown in the graph of FIG. 6. In this situation, only ions within a very narrow range of $K_2$ are transmitted. The compensation voltages C can be altered to set the actual $K_2$ value for transmission. The compensating voltages can be scanned to produce a high-field spectrum. This could be regarded as a parallel motion spectrometer since the direction of ion extraction in the same as that of the analysis field.

Figure 7:
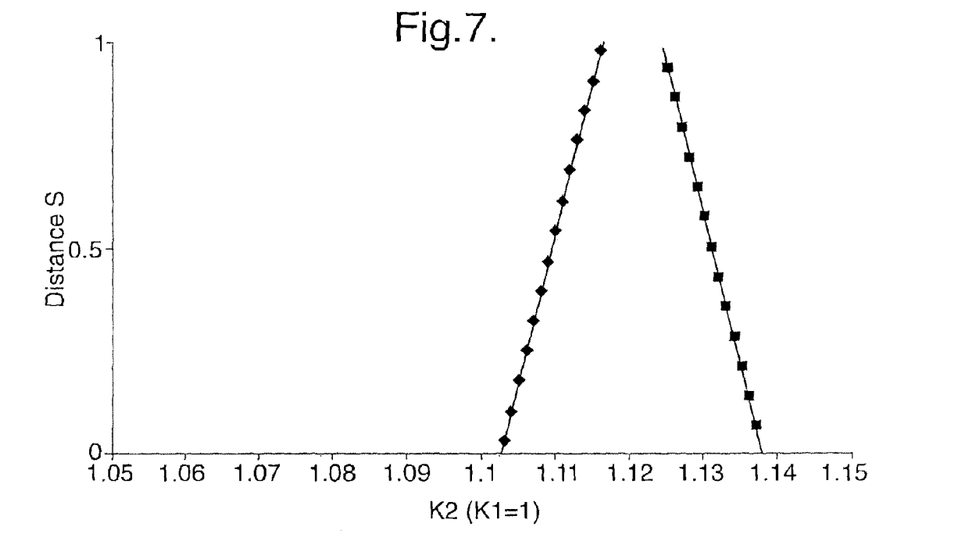
FIG. 7 is a graph similar to that in FIG. 6 but with the one of the compensating voltages adjusted to increase the width of the band pass.

In addition, the resolution of such a combined device may be adjusted by varying one or both of the compensation voltages. In the arrangement shown in FIG. 7, for example, a broader range of ions is selected simply by adjusting one of the compensation voltages C to increase the pass-band.

Figure 8:
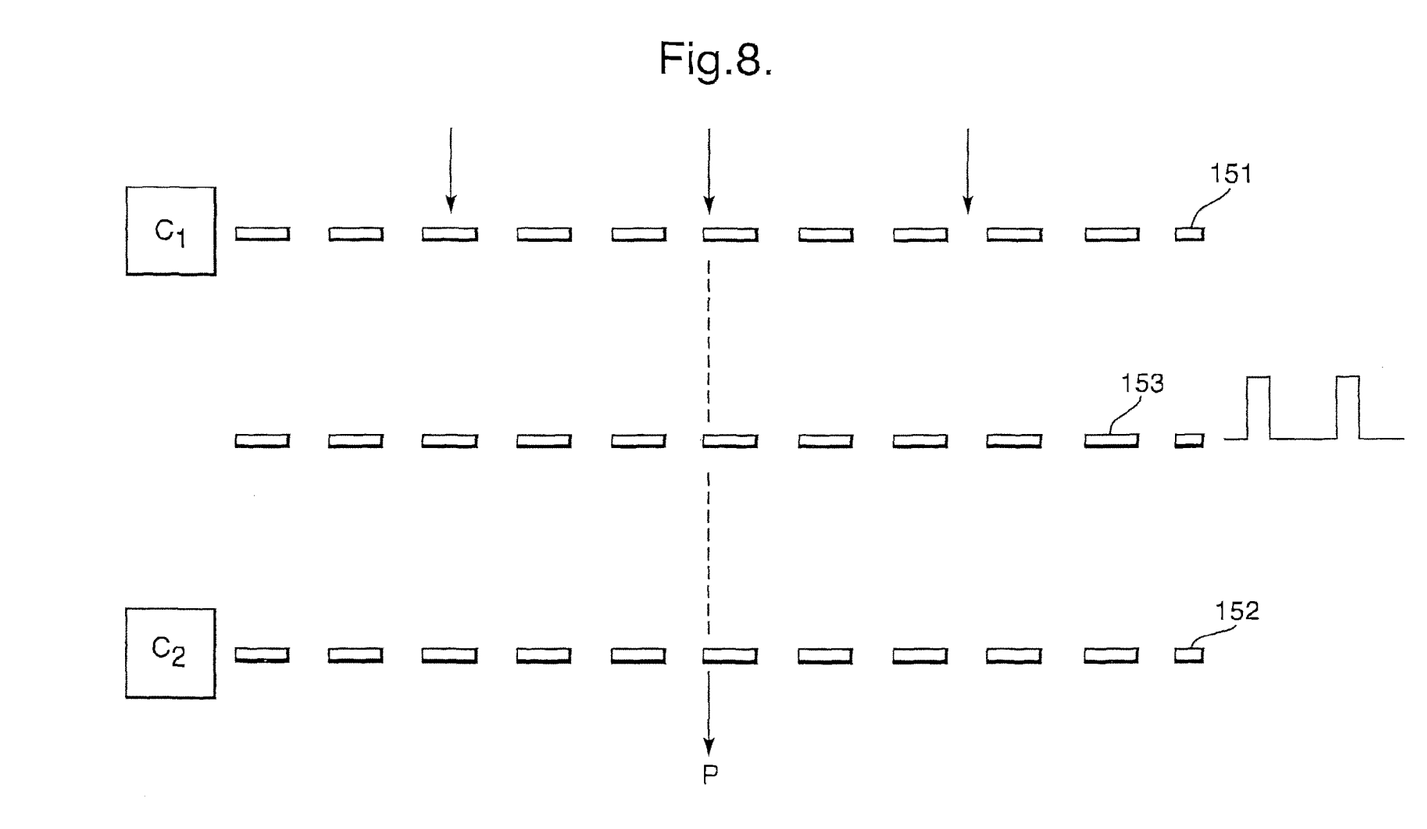
FIG. 8 shows schematically an electrode arrangement by which the combined arrangement shown in FIGS. 6 and 7 could be implemented.

FIG. 8 shows how a combined system could be implemented having three grid electrodes 151, 152 and 153, with two independent compensation voltages (C1 and C2) applied to the outer electrodes 151 and 152 and one asymmetric waveform applied to the middle electrode 153.

If the grid structures described above were used with bulk gas flowing through the grid electrodes, it is possible operation of the mobility selection could be disturbed, although in practice this would not seem to be a problem.

Consider a typical gas flow of 240 $cm^3 \cdot min^{-1}$ flowing through a grid with an area 1 $cm^2$, then the average velocity of the gas is about $^4 cm \cdot sec^{-1}$. In a conventional time-of-flight IMS, the low-field ion velocity for a fairly massive ion might be about 500 $cm \cdot sec^{-1}$ for a field of 200 $v \cdot cm^{-1}$. The ion velocity is comparable with the gas velocity at fields around 2 $v \cdot cm^{-1}$. For a device with an analytical gap around 0.5 mm, a field of 2 $v \cdot cm^{-1}$ corresponds to a potential difference (compensation voltage) of 0.1 volts. A typical compensation voltage for a high field device might be 5 volts so, even if the gas flow were to stop entirely, it would only cause a 2% change in the required compensation voltage.

The arrangement of the present invention has the advantage of requiring only relatively simple structures, which are readily constructed. The resolution of the device can be adjustable electronically. The arrangement can be compatible with time-of-flight ion mobility spectrometers and could form the first stage in a combined instrument.

In these systems, the time taken for the ion to travel through the device is dependent on, amongst other things, the differential mobility. An alternative high field spectrometer could be produced where a pulse of ions is admitted to the spectrometer so that its output is a spectrum where the time of arrival of the ion was inversely proportional to its differential mobility.

The asymmetric field applied substantially parallel to the ion flow path need not be used to filter or remove completely ions but could be used to alter the time taken by ions to reach the detector. In the arrangement shown in FIG. 9 a time shift analyzer 106 located to the right of a gate 104 is arranged to measure changes in ion mobility when ions are subjected to electric fields of different magnitudes. The analyzer 106 includes two grid electrodes 107 and 108 extending laterally of the housing 101, that is, at right angles to the axial flow path of the ions from left to right along the apparatus. The grid electrodes 107 and 108 extend parallel to one another and are closely spaced, typically by a distance of about 0.5 mm. The two electrodes 107 and 108 are electrically connected outside the housing 1 with an electrical drive unit 110 arranged to apply an asymmetric voltage between the two electrodes. An output is provided by the detector plate 111.

A waveform of the kind shown in FIG. 3 is applied between the two electrodes 107 and 108 to cause the ions to oscillate. Ignoring any difference in mobility at high fields, the distance moved by the ions is dependent on a product of the voltage and the time interval for which the voltage is applied. The time intervals of the low voltage period is made longer than that of the high voltage period such that the distance travelled by an ion during the high field period is the same as that travelled in the opposite direction during the longer low field period. The alternating field by itself, therefore, results in no change in the mean position of those ions that do not have field-dependent mobilities. Where, however, the mobility does vary with field strength, there is a difference in the distance travelled by the ions during the high-field and low-field parts of each cycle, causing a change in the mean position of the ions.

The mean position of the field-dependent ions will, therefore, change gradually at a rate determined by the magnitude of the high and low fields and on the field-dependent changes in the mobility of the particular ion.

Where the mobility does not vary with electric field, that is, $K_1 = K_2$, $$S = K_2(E_1 \cdot t_1 + E_2 \cdot t_2), \text{ or}$$

$$S = K_2(V_1 \cdot t_1/D + V_2 \cdot t_2/D) = K_2(V_1 \cdot t_1 + V_2 \cdot t_2)/D$$

So: $S=0$

Where, however, mobility is dependent on the magnitude of the field, the ion will traverse the gap D between the grids 7 and 8 in N cycles of the waveform:

$$N \cdot S = D$$

The time T taken is given by:

$$T = N \cdot (t_1 + t_2)$$

Where $N=D/S$ $$N=D/(K_1 \cdot E_1 \cdot t_1 + K_2 \cdot E_2 \cdot t_2)$$

Given that $V_1 \cdot t_1 = -V_2 \cdot t_2, E_1 = V_1/D$ and $E_2 = V_2/D$, $$E_1 \cdot t_1 = V_1 \cdot t_1/D$$

and $E_2 \cdot t_2 = -V_1 \cdot t_1/D$ so $N=D/(K_1 \cdot V_1 \cdot t_1/D - K_2 \cdot V_1 \cdot t_1/D)$ or $N=D^2/V_1 \cdot t_1(K_1-K_2)$ Hence, the time taken is given by:

$$T=D^2(t_1+t_2)/V_1 \cdot t_1(K_1-K_2)$$

Figure 9:
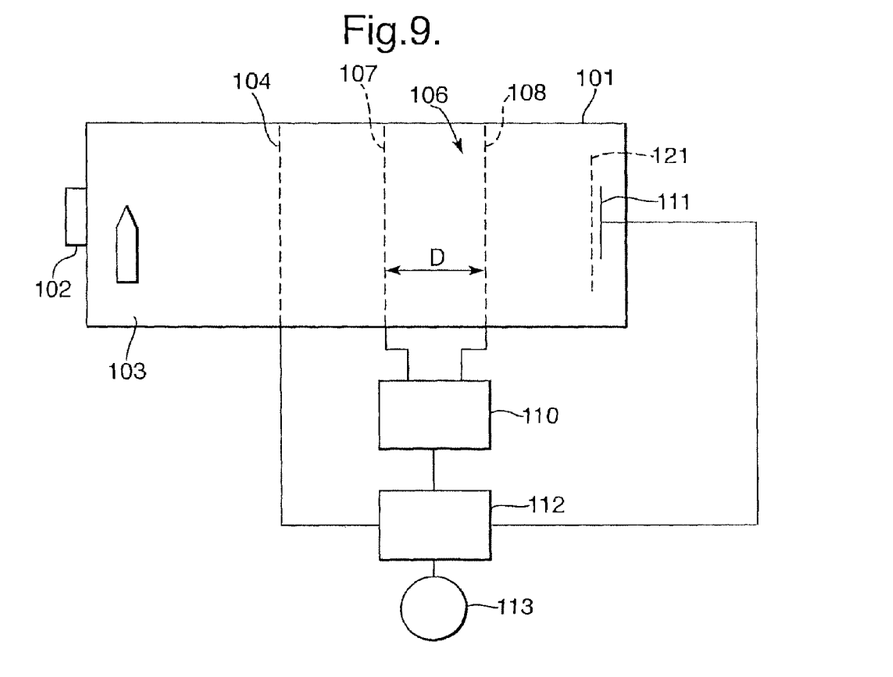
FIG. 9 shows schematically a modification of the system.

So, the time taken for an ion to travel between the grids 107 and 108 is proportional to the square of the grid spacing D, is inversely proportional to the difference between the high-field and low-field mobilities and is inversely proportional to the voltage applied.

The apparatus may include several time shift analysers arranged one after the other provided by a series of pairs of grid electrodes, in order to introduce a greater difference between the time taken by field-dependent ions to reach the detector 11 than non-field dependent ions. In some applications it may be necessary to reverse the polarity of the high and low voltages so that the voltage on one grid electrode is positive and that on the other electrode is negative.

There are various methods in which this apparatus can be operated.

In the first arrangement, a pulse of several different ion species to admitted by the gate 104 to the analyser 106. Signals are produced at the detector plate III at different times dependent on the differences between the low field mobility and the high field mobility of respective ions. This simple arrangement can be used to measure differences in mobility, which are compared in the processor 112 with stored data of the mobility differences of known substances. In this way the chemical composition of a substance or mixture can be determined, or the presence or absence of a substance of interest can be determined.

A problem with the first arrangement outlined above is that it does not allow detection of two classes of ions, namely, those that have a mobility that is invariant with electric field and those ions that do have a field-dependent mobility but where the asymmetric field causes them to travel back towards the gate 104. It is possible to identify the second class of ions simply by reversing the field but this does not enable ions that do not have a field-dependent mobility to be identified. In order to overcome this problem a static electric field component could be added to ensure that all ions pass through the analyser 106 and arrive at the detector plate 111. This could be achieved by adding a static, dc component to the voltages applied across the grid electrodes 107 and 108 or this dc component could be added via separate electrodes.

There are various different ways in which the static field could be employed. In one method the asymmetric field is switched off so that only a dc field is applied and the ions move to the detector plate 111 in the same manner as in a conventional IMS instrument. The output of the detector plate 111 then provides an indication of the low field mobility of the ions. The asymmetric field is then switched on and the times of arrival of the ions is measured. The difference between the times in these two field conditions indicates how mobility changes with electric field.

The addition of the compensation voltage C modifies the time T taken as follows:

$$T=D^2 \cdot (t_1+t_2)/\{V_1 \cdot t_1(K_1 \cdot K_2) + C \cdot (K_1 \cdot t_1 + K_2 \cdot t_2)\}$$

So, when the high-field and low-field mobilities are the same, that is $K_1=K_2$, the $K_1-K_2$ term disappears and the time T is defined by the mobility of the ion and the magnitude C of the dc field.

An alternative method relies on suitable adjustment of the value C of the dc field component. The value of C is set initially to be small (Ca) but such that all the ions of interest pass through the device with the asymmetric field off. The times of arrival of the ions are detected and stored in the processor 112. The drive unit 110 then switches on the asymmetric field and the value of C is adjusted successively for each ion type such as to bring the arrival time of that ion back to what it was with the asymmetric field switched off. This new value of C (say Cb) is stored in the processor 112 for each ion; the difference between Ca and Cb is a measure of how the ion mobility changes with electric field. Again, the processor 112 can use this to identify the nature of the ions by comparison against a stored table of mobility change for different substances.

Figure 10:
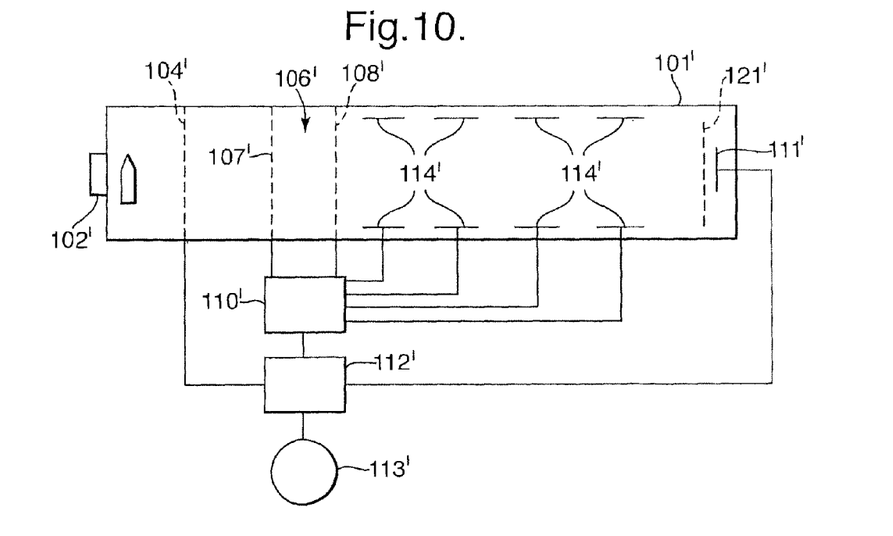
FIG. 10 shows a modification of the arrangement of FIG. 9.

The apparatus shown in FIG. 9 may be used by itself to obtain information about ions. It may also be combined with other forms of detector in order to provide additional enhanced information. For example, the apparatus can be readily combined with a conventional time-of-flight ion mobility spectrometer operating to measure the mobility of ions under low field conditions. Most conveniently, as shown in FIG. 10, the IMS function can be combined with the field-dependent apparatus in the same housing 101' between the electrodes 107' and 108' of the time shift analyser 106' and the detector plate 111'. This may be achieved simply by providing a number of additional electrodes 114' spaced from one another along the housing 101' and connected to a drive unit 110' arranged to apply voltages to the electrodes that are progressively higher towards the detector plate. In this way, an increasing dc field is established to propel the ions towards the detector plate 111'.

Various other modifications are possible to the apparatus.

The apparatus could include an ion-molecule reaction region between the ion source and the gate. In this region the primary ions produced by the source are allowed to mix with non-ionized molecules of the gas being analysed.

It is not essential for the apparatus to have an ion gate to control admission of the ions to the analyser. By scanning the dc voltage C in magnitude, ions with different differential mobilities will arrive at the detector plate successively. Differentiating the detector signal gives a spectrum of differential mobilities. If a low frequency, low voltage, alternating potential were applied in addition to the dc voltage, it would be possible to measure the magnitude of this frequency component in the signal at the detector plate without the need for differentiating.

If the asymmetric waveform is of sufficient magnitude, ion modification may occur in the manner described in GB0508239.1. This leads to additional ions, which further facilitates positive identification of the analyte substance. This modification may be as a result of removal of dopant adducts or break up of the ion itself and the production of daughter species. The analyser itself may be used to cause this ion modification or a separate ion modification region could be included before or after the time shift analyser.

What is claimed is:

1. A spectrometer comprising:
an ion filter including:
one or more electrodes comprising wire grids with spaces between wires though which ions can pass,
wherein the one or more electrodes are configured to apply an asymmetric field, spaced along a path which ions are to travel in a drift region, said electrodes being arranged so the ions experience high and low voltages of the asymmetric field when passing through the ion filter, and
wherein the ion filter is configured to pass selected ones of the ions to a detector.

2. The spectrometer of claim 1 wherein the ion filter is configured so that ions experience the low voltage longer than the high voltage.

3. The spectrometer of claim 1, wherein the drift region is configured to operate substantially at ambient pressure.

4. The spectrometer of claim 1, wherein the high and low voltages have different polarities.

5. The spectrometer of claim 1, wherein the ion filter is further configured to cause at least some of the ions to travel away from the detector.

6. The spectrometer of claim 1, wherein said electrodes are perpendicular to the path.

7. The spectrometer of claim 1, wherein the ion filter is further configured to prevent ions other than the selected ones if the ions included in the ions from being detected.

8. The spectrometer of claim 1, wherein the ion filter is further configured to cause at least some of the ions to travel a net distance in accordance with:

$$S=K_1 * E_1 * t_1 + K_2 * E_2 * t_2$$

wherein:
S is equal to the net distance traveled by a respective ion of the at least some ions,
$K_1$ is the respective ion's ion mobility in the low field,
$E_1$ is the amplitude of the low field,
$t_1$ is time spent by the respective ion in the low voltage,
$K_2$ is the respective ion's ion mobility in the high voltage,
$E_2$ is the amplitude of the high field, and
$t_2$ is time spent by the respective ion in the high voltage.

9. The spectrometer of claim 1, wherein the ion filter is further configured to cause the spectrometer to discriminate between ions that are field-dependent and ions that are not field-dependent, wherein the ions that are field-dependent and the ions that are not field-dependent would produce similar output by the detector absent inclusion of the ion filter.

10. The spectrometer of claim 1, wherein the ion filter is further configured to apply a compensation voltage to at least one of oppose or reinforce motion of at least some of the ions along the path.

11. The spectrometer of claim 1, wherein the ion filter is operable to cause the spectrometer to discriminate between ions that have different field-dependency levels.

12. An ion filter for a spectrometer, the ion filter comprising:
a first electrode configured to apply an asymmetric field across a path along which ions are to travel towards a detector; and
at least two other electrodes, disposed on opposite sides of the first electrode along the path, said other electrodes being configured to, respectively, apply a compensation voltage parallel with the path, wherein the ion filter is operable to facilitate discrimination between selected ones of the ions and other ions of the ions that, absent inclusion of the ion filter in a spectrometer, would result in similar detector output,
the first electrode and the at least two other electrodes comprising a grid with gaps therein through which the selected ones of the ions can pass.

13. The ion filter of claim 12, wherein the spectrometer comprises an ion mobility spectrometer.

14. The ion filter of claim 12, wherein the ion filter is further configured to prevent detection of the other ions when the ion filter is included in the spectrometer.

15. The ion filter of claim 12, wherein the ion filter in operation is configured to cause the selected ones of the ions to experience a lower voltage of the asymmetric field longer than a higher voltage of the asymmetric field.

16. The ion filter of claim 12, wherein the ion filter is configured to facilitate discrimination of respective ions of the ions based on whether an ion mobility of the respective ions is field-dependent.

17. The ion filter of claim 12, wherein the ion filter is configured to facilitate discrimination between ions that have different field-dependency levels that, absent inclusion of the ion filter in a spectrometer, would result in similar detector output.

18. The ion filter of claim 12, wherein the ion filter in operation opposes or reinforces motion of at least some of the ions along the path.

19. The ion filter of claim 12, wherein higher and lower voltages of the asymmetric field have different polarities.

20. A method comprising:
applying an asymmetric field along a path which ions are to travel in a drift region via electrodes comprising a grid with gaps therein through which the selected ones of the ions can pass;
providing a compensation voltage along the path so selected ones of the ions experience a lower voltage of the asymmetric field for a longer period of time than a higher voltage of the asymmetric field;
passing the selected ones of the ions to be detected.

21. The method of claim 20, further comprising repeating the applying of the asymmetric field and the providing the compensation voltage to provide alternating periods in which ions passing to the detector experience the asymmetric field.

22. The method of claim 20, further comprising reversing the polarity of the asymmetric field.

23. The method of claim 20, further comprising directing at least some of the ions away from a detector.

24. The method of claim 20, wherein the polarity of the higher voltage is opposite the polarity of the lower voltage.

* * * * *